(12) United States Patent
Ewers et al.

(10) Patent No.: US 8,092,489 B2
(45) Date of Patent: Jan. 10, 2012

(54) TISSUE GRASPING APPARATUS

(75) Inventors: Richard C. Ewers, Fullerton, CA (US);
Eugene Chen, Carlsbad, CA (US);
Arvin T. Chang, West Covina, CA (US);
Robert A. Vaughan, Laguna Niguel, CA (US)

(73) Assignee: USGI Medical, Inc., San Clemente, CA (US)

(*) Notice: Subject to any disclaimer, the term of this patent is extended or adjusted under 35 U.S.C. 154(b) by 464 days.

(21) Appl. No.: 11/736,539

(22) Filed: Apr. 17, 2007

(65) Prior Publication Data
US 2008/0262539 A1 Oct. 23, 2008

(51) Int. Cl.
*A61B 17/28* (2006.01)
(52) U.S. Cl. .................................... 606/208
(58) Field of Classification Search ........... 606/139, 606/142, 144, 151, 153, 157, 205–211
See application file for complete search history.

(56) References Cited

U.S. PATENT DOCUMENTS

| | | |
|---|---|---|
| 3,628,522 A | 12/1971 | Kato |
| 4,710,172 A | 12/1987 | Jacklich et al. |
| 5,052,402 A | 10/1991 | Bencini et al. |
| 5,059,214 A * | 10/1991 | Akopov et al. ............... 606/207 |
| 5,263,967 A | 11/1993 | Lyons et al. |
| 5,290,309 A * | 3/1994 | Kothe ............................ 606/207 |
| 5,312,434 A | 5/1994 | Crainich |
| 5,366,477 A | 11/1994 | LeMarie et al. |
| 5,409,478 A | 4/1995 | Gerry et al. |
| 5,609,599 A * | 3/1997 | Levin ............................ 606/153 |
| 5,618,307 A | 4/1997 | Donlon et al. |
| 5,624,431 A | 4/1997 | Gerry et al. |
| 5,665,105 A | 9/1997 | Furnish et al. |
| 5,797,956 A | 8/1998 | Furnish et al. |
| 5,810,876 A | 9/1998 | Kelleher |
| 6,013,095 A | 1/2000 | Ouchi |
| 6,666,876 B2 * | 12/2003 | Kawai et al. .................. 606/205 |
| 7,186,261 B2 | 3/2007 | Prestel |
| 2005/0119671 A1 * | 6/2005 | Reydel et al. ................. 606/144 |
| 2005/0251161 A1 * | 11/2005 | Saadat et al. .................. 606/153 |
| 2005/0251166 A1 * | 11/2005 | Vaughan et al. .............. 606/153 |

* cited by examiner

*Primary Examiner* — Kevin T Truong
(74) *Attorney, Agent, or Firm* — Levine Bagade Han LLP

(57) ABSTRACT

A tissue grasping apparatus includes a control member, an elongated shaft, and a tissue grasping member attached to the distal end of the elongated shaft. An activation mechanism provides an user-operable connection between the control member and the tissue grasping member. In an embodiment, the tissue grasping member includes a pair of jaws configured to open to an included angle between the jaws of 180 degrees or more. In an embodiment, the activation mechanism includes a flexible drive wire attached to the penetrating member.

11 Claims, 15 Drawing Sheets

TISSUE GRASPING APPARATUS

RELATED APPLICATION DATA

None.

FIELD OF THE INVENTION

The present invention relates to surgical instruments used to engage, grasp, or manipulate tissue, and methods of their use.

BACKGROUND OF THE INVENTION

Tissue engaging, grasping, and manipulating instruments are used during open surgery, laparoscopic surgery, endoscopic surgery, or translumenal surgery. A common type of instrument available for endolumenal acquisition of stomach tissue is an endoscopic grasper. A typical endoscopic grasper includes a pair of hinged jaws located at the distal end of a flexible shaft. The jaws are actuated between open and closed positions. Typically, the jaws are actuated using a push/pull rod or wire that extends through the flexible shaft to connect to the jaws via a mechanical linkage. When the jaws are opened, they assume a wide "V" shape. The jaws are then brought into contact with tissue, after which the jaws are actuated to the closed position. Closing the jaws causes the jaws to catch on, pinch, or entrap the tissue.

Conventional hinged jaw-type endoscopic graspers like those described above have several limitations. For example, the mechanical linkages used to actuate the jaws in typical endoscopic graspers are unable to drive the jaws open to or beyond an included angle (the angle formed between the jaws) of 180 degrees. This limitation reduces the effectiveness of these graspers in circumstances in which a wider throw (having an included angle equal to or greater than 180 degrees) is desirable. In addition, the mechanical linkages must be configured such that they do not reach a point of linear alignment during actuation to the closed position, otherwise the closure force will drop to zero and the jaws will be inoperable.

Another common type of endoscopic grasper includes two or more spring biased jaws that are actuated using an external sleeve. The jaws comprise flats of spring steel that have opposing curved or angled surfaces that have a spring bias toward the open position relative to one another. The external sleeve is slidable over the jaws. As the external sleeve is translated distally toward the ends of the spring biased jaws, the external sleeve causes the jaws to move toward one another to the closed position.

The foregoing spring jaw-type of endoscopic grasper also has limitations. For example, the jaws of these types of graspers open passively, i.e., they open only due to and are only as strong as the inherent spring force between the jaws. They are, therefore, not well suited to open fully in constrained spaces where surrounding tissue could retard the spring open force. Also, the closure requires a relative motion that makes targeting of a selected portion of tissue (or other target) difficult due to the relative movement (e.g., retraction) of the jaws into the external sleeve. Further still, the closure force of the jaws reaches its peak as the jaws are being retracted fully into the external sleeve, at which point the jaws are unable to grasp tissue.

Yet another type of endoscopic grasper includes a tissue piercing coil member attached to the distal end of a flexible shaft. The coil member has a sharp tip and an open pitch that allows the coil member to penetrate tissue when it is rotated against the tissue with a light amount of distal force. Once tissue is penetrated, the grasper allows the user to manipulate the tissue by advancing or retracting the grasper.

The coil-type grasper has limitations in that it only grasps a single point of tissue, and cannot easily grasp or bring together multiple contact points or grasp a relatively large area of tissue. The coil-type grasper also achieves its grasp by a "blind" penetration of tissue by the coil.

SUMMARY

In one general aspect, a medical instrument according to the present invention includes a tissue grasping member configured for introduction into a patient. The medical instrument is adapted for use during open surgery, laparoscopic surgery, endoscopic surgery, or translumenal surgery. In several preferred embodiments, the medical instrument has a small profile such that the tissue grasping member is able to pass through a small diameter lumen to be routed to a site within a patient's body. In several other preferred embodiments, the medical instrument has an elongated, flexible shaft that allows the instrument to be passed through tortuous anatomy, either as a standalone instrument or as an instrument to be passed through a lumen of an overtube. The tissue grasping member is used to engage, grasp, acquire, position, or otherwise manipulate tissue within a patient. The medical instrument is suitable for use as a standalone instrument, or it may be used in combination with other instruments that provide independent or related functions.

In one embodiment, the medical instrument includes a tissue grasping member attached to the distal end of a shaft. A control member, such as a handle, is provided at the proximal end of the instrument, preferably coupled to the proximal end of the shaft. The control member serves as an interface for the user to manipulate or control the action of the tissue grasping member. An activation mechanism is provided at or near the distal end of the shaft and is operatively connected to the control member. In an embodiment, the activation mechanism is adapted to translate manipulations of the handle by the user into movement of the tissue grasping member.

The tissue grasping member is adapted to grasp tissue presented in a concave orientation more effectively than conventional endoscopic grasping instruments. In several embodiments, the tissue grasping member is provided with a pair of jaws that are configured to move to an open position that defines an included angle between the contact surfaces of the jaws that is equal to or greater than 180 degrees. In several embodiments, the tissue grasping member includes at least one vertex tooth formed on the contact surface of a jaw, the vertex tooth forming an included angle of less than 90 degrees relative to the contact surface of the jaw. The vertex tooth is thereby configured to grasp and pull tissue into the jaws of the tissue grasping member, improving the ability of the tissue grasping member to engage, grasp, and manipulate tissue.

BRIEF DESCRIPTION OF THE DRAWINGS

FIG. 8B illustrates an inverted tissue fold. FIG. 8C illustrates an everted tissue fold.

DETAILED DESCRIPTION

Figure 1A:
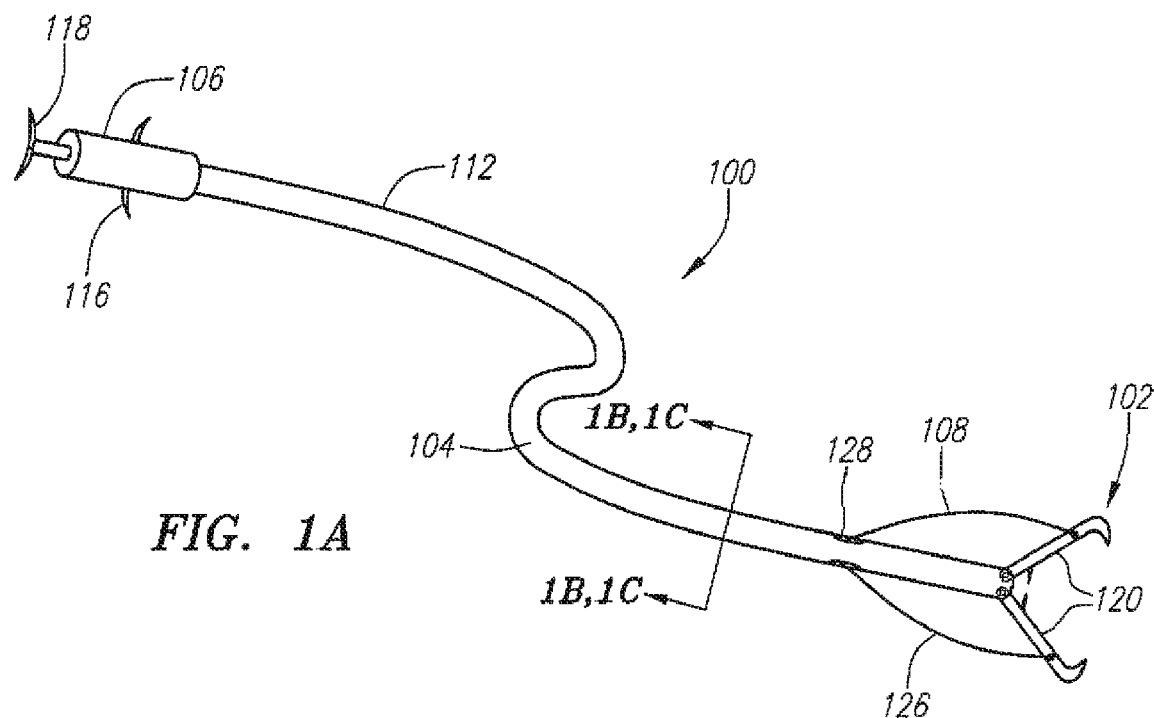
FIG. 1A is a perspective view of a medical instrument having a tissue grasping member in accordance with the present invention.

Referring to FIG. 1A, a first embodiment of a medical instrument 100 for engaging, grasping, or manipulating tissue is shown. In several embodiments, the medical instrument is configured to be able to pass through a relatively small diameter lumen such as the surgical tool lumens provided during laparoscopic, endoscopic, or translumenal surgery. In other embodiments, the instrument is configured for use during conventional open surgery, or other procedures in which the size restraints required during laparoscopic, endoscopic, or translumenal surgery are not present. The medical instrument shown in FIG. 1A includes a tissue grasping member 102 attached to the distal end of a shaft 104. A control member, such as a handle 106, is provided at the proximal end of the instrument, preferably coupled to the proximal end of the shaft 104. The control member serves as an interface for the user to manipulate or control the action of the tissue grasping member 102. An activation mechanism 108 is provided at or near the distal end of the shaft 104 and is operatively connected to the control member. In the embodiment shown in FIG. 1A, the activation mechanism 108 is adapted to translate manipulations of the handle 106 by the user into movement of the tissue grasping member 102.

Figure 1B:
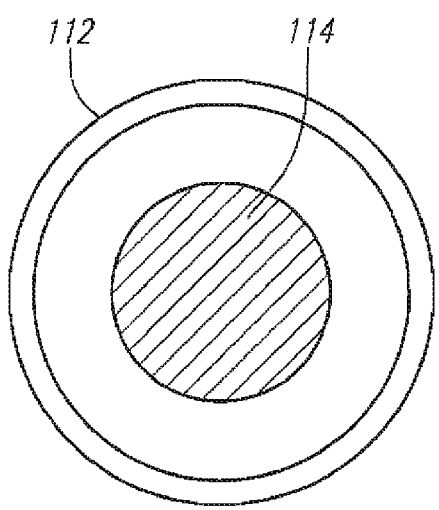
FIGS. 1B and 1C are cross-sectional views of two embodiments of a shaft in accordance with the medical instrument shown in FIG. 1A.

In an embodiment, the shaft 104 is an elongated, flexible member having an external sleeve 112 and an internal pusher 114. (See FIGS. 1B and 1C). The sleeve 112 and pusher 114 are capable of longitudinal motion relative to one another. For example, in an embodiment, the sleeve 112 is cylindrical, defining an internal lumen in which the pusher 114 is located. The pusher is longitudinally translatable within the external sleeve, preferably slidably, thereby providing the capability for the external sleeve 112 and pusher 114 to move longitudinally relative to one another.

The external sleeve 112 is adapted to provide a flexible, operable interconnection between the handle 106 and the tissue grasping member 102. In an embodiment, the external sleeve 112 is formed of materials having sufficient strength and other materials properties to support transmission of torque forces between the handle 106 and the tissue grasping member 102. For example, the external sleeve 112 is capable of causing the tissue grasping member 102 to rotate around the longitudinal axis of the shaft 104 in response to a rotation of the handle 106. In an embodiment, the external sleeve 112 also supports relative sliding movement of the pusher 114 within the sleeve with very little friction and without a large amount of longitudinal stretch or contraction of the shaft 104. In an embodiment, the external sleeve 112 is constructed of a single material. In another embodiment, the external sleeve 112 has a composite construction that includes two or more of a main body material to provide structure and/or flexibility, a reinforcing material to provide torque transmission capability and/or to reduce or eliminate stretch and contraction, and a liner material to provide structure, to reduce friction, and/or to reduce or eliminate stretch and contraction. Examples of materials that are suitable for forming the main body portion of the external sleeve include polymeric materials, such as polyester amide block copolymer (PEBAX™), nylon, polyurethane, or other similar materials commonly used for medical instrument applications. Examples of suitable reinforcing materials include polymeric or metallic braid materials and/or reinforcing wires. Examples of suitable liner materials include polytetrafluoroethylene (PTFE), polyetheretherketone (PEEK), or other suitable materials.

Figure 1C:
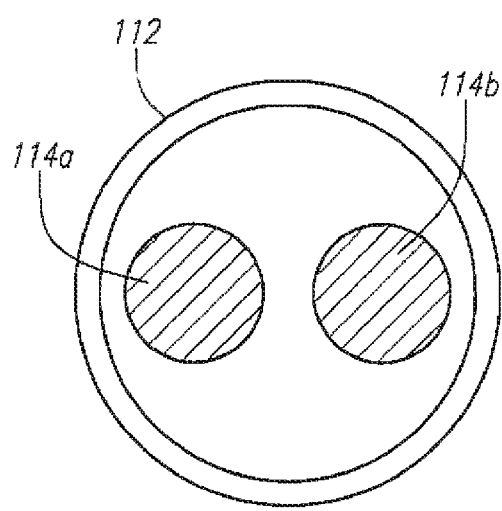

The pusher 114 is adapted to transfer a longitudinally-directed force applied by the user from the handle 106 to the tissue grasping member 102. In the embodiment shown in FIG. 1B, the pusher 114 is formed of a single solid wire or similarly-shaped member that extends through the length of the lumen formed by the external sleeve 112. As described above, the pusher 114 and external sleeve 112 are adapted to move longitudinally relative to one another. In an embodiment, the pusher 114 is a wire formed of stainless steel, nickel titanium alloy (Nitinol), or other material commonly used for medical instrument applications. In other embodiments, the pusher 114 is formed of non-continuous segments aligned end-to-end and joined together to provide the desired longitudinal translation force. In still other embodiments, shown in FIG. 1C, the pusher 114 comprises two or more continuous or non-continuous wires, rods, or similarly-shaped members 114a, 114b. In some embodiments, the two or more members are arranged coaxially within the sleeve 112, while in other embodiments the two or more members 114a, 114b are aligned alongside one another, as shown in FIG. 1C.

The handle 106 is configured to provide relative movement between the external sleeve 112 and the pusher 114 associated with the shaft 104. Several common types of medical instrument handles are suitable for this purpose. In FIG. 1, the medical instrument 100 is illustrated with a syringe-type handle 106 having a main body 107 connected at its distal end to the proximal end of the external sleeve 112, and a pair of finger tabs 116 extending from opposite sides of the main body 107. A thumb tab 118 is attached to the pusher 114 and extends out of the proximal end of the handle main body 107. The syringe-type handle 106 is a common handle used in medical instruments that require relative movement between a pair of shafts or a sleeve and pusher, such as the present device. Other handle types are suitable for use as well, as will be recognized by a person having skill in the art. For example, in other embodiments, the handle includes either a pistol grip, a grip having tabs and a thumb plunger, or other structures. In still other embodiments, the handle includes a spring providing a biasing force between the sleeve 112 and the pusher 114, the spring causing the tissue grasping member 102 to be biased to an open or closed position. In still other embodiments, the handle 106 includes an indexing mechanism to selectively open or close the tissue grasping member 102 to one or more predetermined positions. In still other embodiments, the handle 106 includes a locking mechanism to selectively lock the tissue grasping member 102 in a selected position.

Figure 1D:
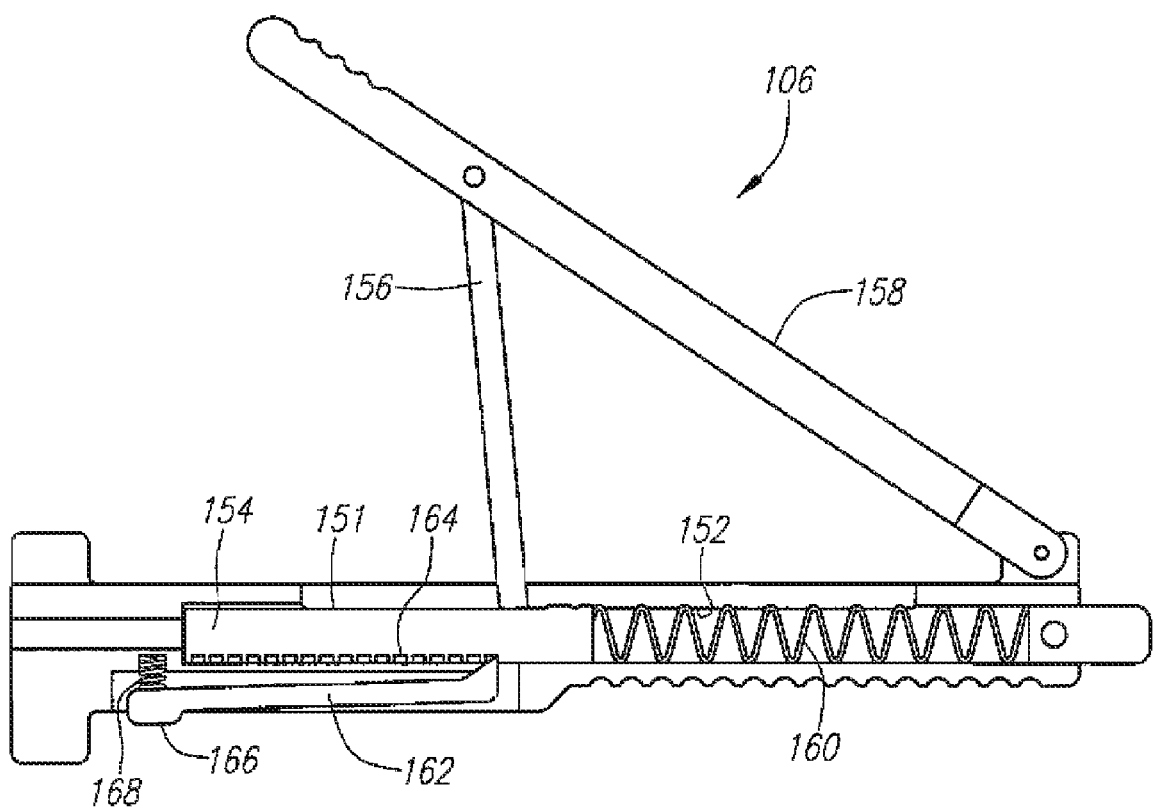
FIG. 1D is a cross-sectional view of a handle suitable for use with the medical instrument shown in FIG. 1A.

Turning to FIG. 1D, another embodiment of a handle 106 is illustrated. The handle 106 includes an elongated main body 150 having a central channel 152 in which a pusher block 154 is slidably received. A link arm 156 extends through a slot 151 formed on the upper surface of the main body in communication with the central channel 152, and is pivotably attached at one end to the upper surface of the pusher block 154, and pivotably attached at its other end to an actuation arm 158. The actuation arm 158 is pivotably attached to the upper surface of the main body 150 near its distal end. A spring 160 is located within the central channel 152 near its distal end, and provides a spring force biasing the pusher block 154 proximally within the channel.

The main body 150 of the handle 106 is attached or otherwise connected to the external sleeve 112 of the shaft 104. The pusher block 154 is attached or otherwise connected to the pusher 114. Accordingly, as the pusher block 154 is advanced (distally) or withdrawn (proximally) within the central channel 152, the pusher 114 is advanced or withdrawn relative to the external sleeve 112. In the embodiment shown, a user applied downward force applied to the actuation arm 158 causes the pusher block 154 to advance (distally) against the force of the spring 160, thereby advancing the pusher 114 within the sleeve 112. When the user applied force on the actuation arm 158 is released, the spring 160 causes the pusher block 154 to withdraw, thereby withdrawing the pusher 114 relative to the sleeve 112. As explained herein, this motion creates the actuation forces controlling the operation of the tissue grasping member 102.

In the embodiment shown in FIG. 1D, a ratchet mechanism is provided on the handle 106 to selectively and releasably restrict the pusher block 154 to move in only a single direction within the main body 152. The ratchet mechanism includes a pawl 162 that is pivotably connected to the bottom surface of the main body 150 of the handle 106, and is adapted to selectively engage one of a plurality of slots 164 formed on the underside of the pusher block 154. A pawl spring 168 is located between the pawl 162 and the handle main body 152 and provides a force biasing the pawl 162 into engagement with the slots 164 on the pusher block 154. When the pawl 162 is engaged with one of the slots 164, the pusher block 154 is unable to move proximally in the central channel 152. The user is able to disengage the pawl 162, thereby releasing the pusher block 154, by applying a force on the release end 166 of the pawl, which is exposed on the underside of the handle main body. The ratchet mechanism may be reversed—i.e., to restrict distal movement of the pusher block 154—by reversing the relative engagement of the pawl 162 with the slots 164 shown in FIG. 1D, as will be recognized by a person skilled in the art. The ratchet mechanism may be used to maintain a releasable opening or closing force on the tissue grasping member 102, as desired.

Figure 2:
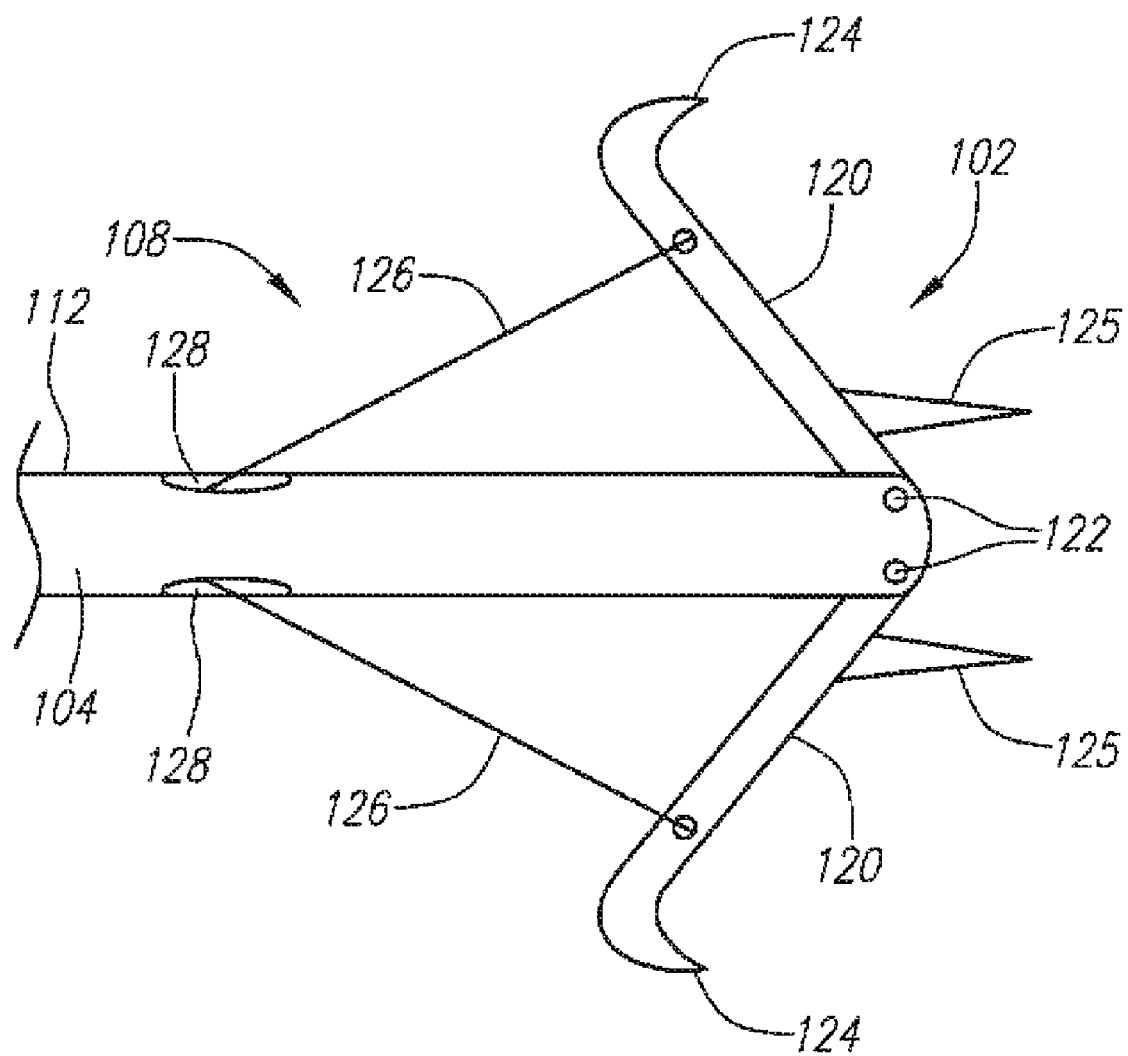
FIG. 2 is a side view of an embodiment of a tissue grasping member and activation mechanism.
Figure 3A:
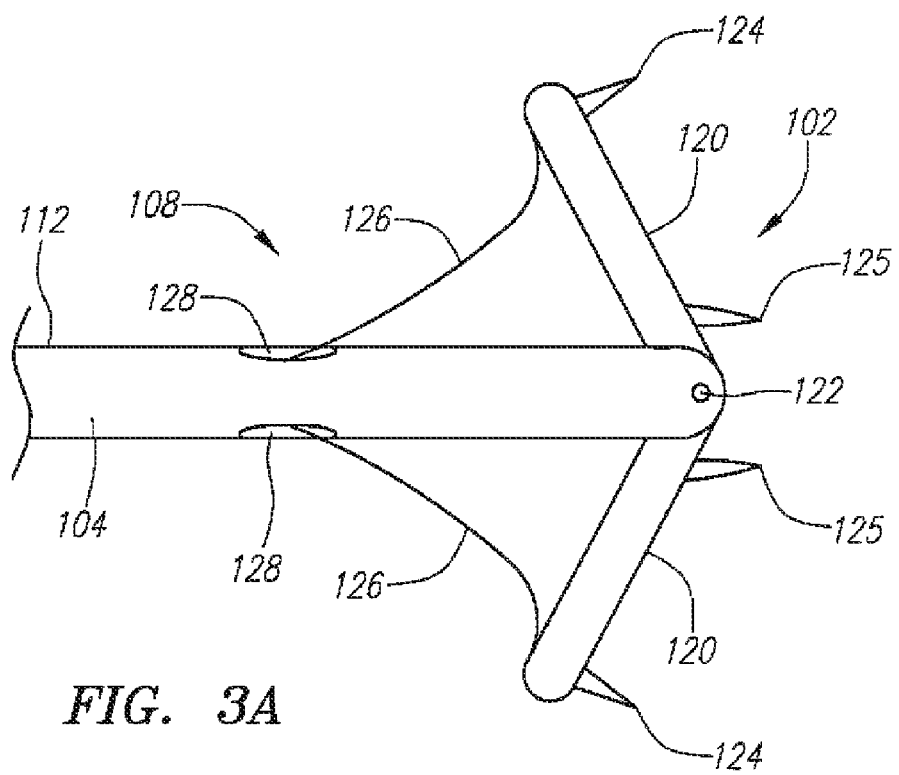
FIGS. 3A and 3B are side views of another embodiment of a tissue grasping member and activation mechanism.
Figure 3B:
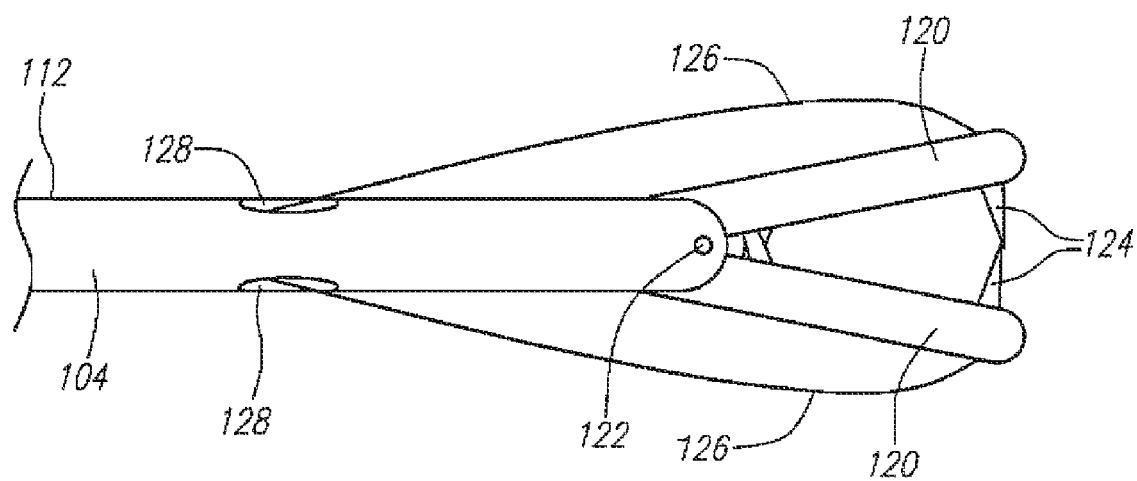

Turning to FIGS. 2 and 3A-B, examples of an activation mechanism 108 and tissue grasping member 102 are shown. The tissue grasping mechanism 102 includes a pair of opposed jaws 120, each of which is pivotably connected with a pin 122 to the distal end of the shaft 104. In the embodiment shown in FIG. 2, each jaw 120 is connected to the shaft 104 by a separate pin 122. In the embodiment shown in FIGS. 3A-B, both jaws 120 are connected by a single pin 122. The jaws 120 are each connected to the distal end of the shaft 104 at a point at or near a first end of each jaw 120. Each jaw 120 is a generally straight, elongate member having a tissue contact side that faces generally in the distal direction when the jaws 120 are in the open position shown in FIG. 2, and a back side that faces generally in the proximal direction when the jaws 120 are in the open position. Each jaw 120 includes one or more engagement members, such as teeth 124, that are located on the tissue contact side of each jaw 120, with the teeth 124 being oriented generally perpendicularly relative to the respective jaws 120. The jaws 120 are configured to be moved between an open position, in which the jaws 120 are rotated proximally about their pivots toward the shaft 104, and a closed position, in which the jaws 120 are rotated distally about their pivots toward one another. The fully closed position corresponds with a position in which the tissue contact sides of each of the jaws 120 are in their distal-most orientation, such as being in close proximity to or in contact with one another.

The engagement members formed on the contact side of the jaws 120 are adapted to enhance or increase the effectiveness of the jaws 120 to engage, grasp, or manipulate tissue. In an embodiment, the engagement members are teeth 124, as shown in the Figures. In other embodiments, the engagement members include serrations, raised or knurled surfaces, roughened surfaces, irregular surfaces, or the like, or any combinations of the same. For clarity, the present description and the Figures are particularly directed to embodiments including teeth 124, with it being understood that other engagement members are also suitable. In several embodiments, the teeth 124 formed on the surface contact side of each jaw 120 include a vertex tooth 125 associated with each jaw 120. Each vertex tooth 125 is located on the contact side of its jaw 120 at a position near the point at which the jaw 120 is attached to the shaft 104. In some embodiments, each vertex tooth 125 is oriented such that it extends from the surface contact side of the jaw at an angle directed inward, i.e., toward the pivotable connection between the jaw 120 and the shaft 104. In these embodiments, the angled orientation of the vertex teeth 125 provide the jaws 120 and the instrument 100 with an alternative capability and method for engaging, grasping, and manipulating tissue The activation mechanism 108 is configured to cause the jaws 120 of the tissue grasping member 102 to move between open and closed positions under control of the handle 106. The exemplary activation mechanisms shown in FIGS. 2 and 3A-B include a pair of drive wires 126, each of which is attached at its distal end to a respective one of the jaws 120. The drive wires 126 extend through a pair of ports 128 formed in the sleeve 112 near its distal end and are attached to the jaws 120 at or near the tips of the jaws 120, i.e., at or near the ends of the jaws opposite the ends at which the jaws 120 are connected to the sleeve 112. In an embodiment, the drive wires 126 are pivotably attached to the jaws 120, such as by a pin, in order to reduce stress in the members at the attachment point. In other embodiments, the drive wires 126 are attached directly to the jaws. In an embodiment, the proximal ends of the drive wires 126 are attached to the pusher 114 within the lumen of the external sleeve 112. In other embodiments, the drive wires 126 extend through all or a portion of the sleeve 112 and are attached directly or indirectly to an operable member associated with the handle 106.

In an embodiment, the drive wires 126 are formed of materials having sufficient strength to move the jaws 120 between the closed and open positions, and to facilitate tissue engagement, grasping, and manipulation, as discussed in more detail below. In addition, the materials used to form the drive wires 126 have sufficient flexibility to allow the drive wires 126 to be routed through the ports 128 formed on the external sleeve 112 and to bow outward to create the closure force, as shown in FIG. 3B. In an embodiment, the drive wires 126 are formed of stainless steel, nickel titanium alloy (Nitinol), or other material having the foregoing material properties.

In several embodiments, including those shown and described above in relation to FIGS. 2 and 3A-B, the medical instrument 100 is configured such that the jaws 120 are movable between a closed position and a completely open position where the included angle between the jaws 120 is equal to or exceeds 180 degrees. As discussed more fully below, this configuration allows the medical instrument to be used to perform functions during endoscopic, laparoscopic, and translumenal procedures that are more difficult or impossible to perform using the conventional graspers described above.

Figure 4A:
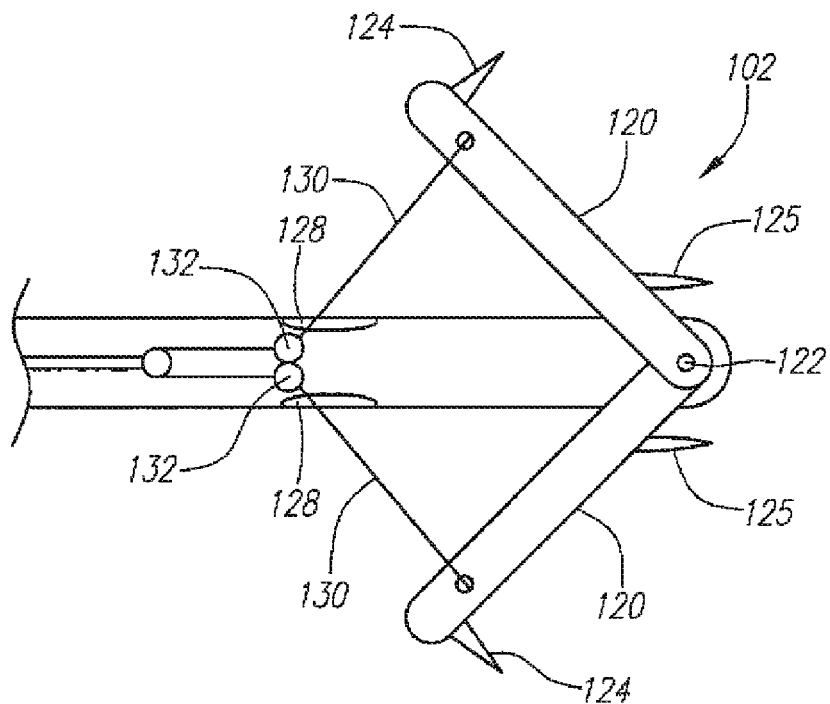
FIGS. 4A and 4B are side views of another embodiment of a tissue grasping member and activation mechanism
Figure 4B:
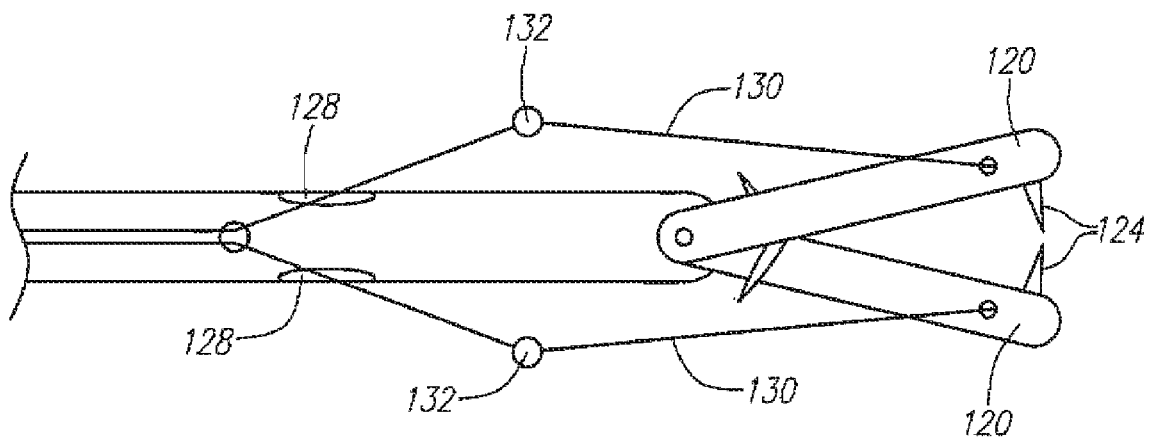

In another embodiment, illustrated in FIGS. 4A-B, the actuation mechanism 108 includes a plurality of links 130 and pivots 132 that provide the actuation force for opening and closing the jaws 120. Each link 130 comprises a rigid member adapted to translate forces to adjacent links by way of the interconnecting pivots 132. The lengths of the links 130 and the locations of the pivots 132 are selected in order to route the actuation mechanism through the ports 128 and to operatively interconnect the pusher 114 with the jaws 120. For example, in an embodiment, the plurality of links 130 includes at least one axially-directed link, at least one transitional link that moves to a substantially off-axis orientation when activated, and at least one terminal link attached to the jaw 120. Accordingly, as the pusher 114 is advanced, the pusher 114 imparts a force to the jaws 120 through the linkage to cause the jaws to move to a closed position. As the pusher 114 is withdrawn, the pusher 114 imparts a force to the jaws 120 through the linkage to cause the jaws to move to an open position. The orientations, sizes, and shapes of the links 130 making up the linkage assembly are able to be optimized to impart a closing force having a mechanical advantage. In an embodiment, one or more rotational stops are provided on one or more of the pivots 132 in order to prevent over-rotation.

Figure 13A:
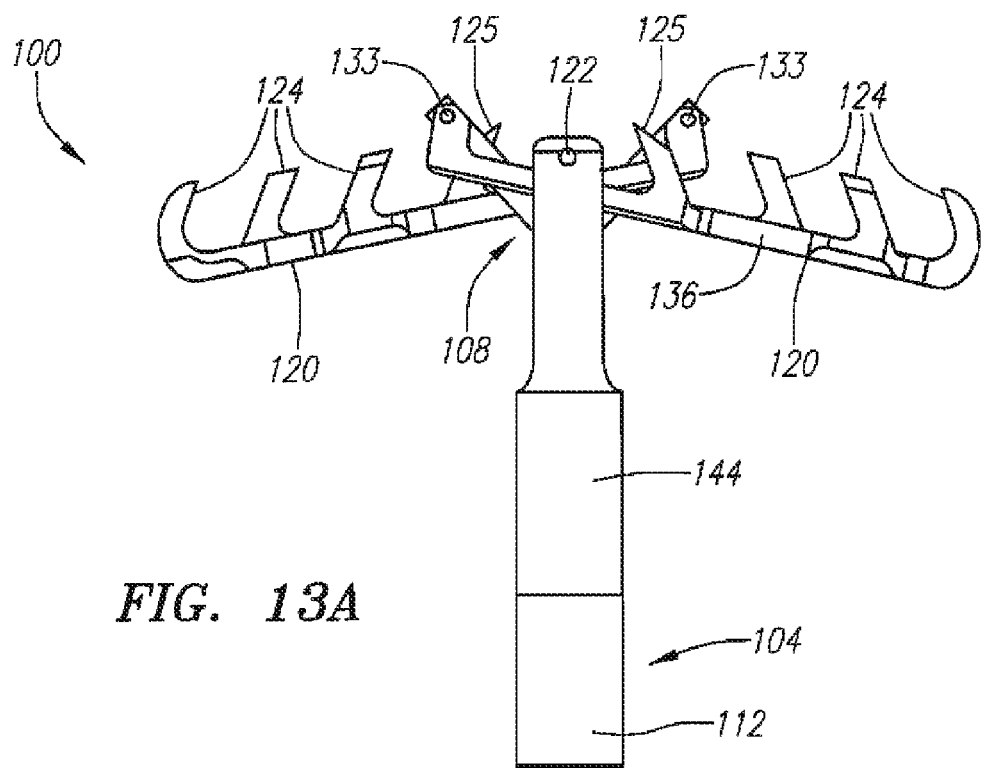
FIGS. 13A-D are side views of another embodiment of a tissue grasping member attached to a shaft.
Figure 13B:
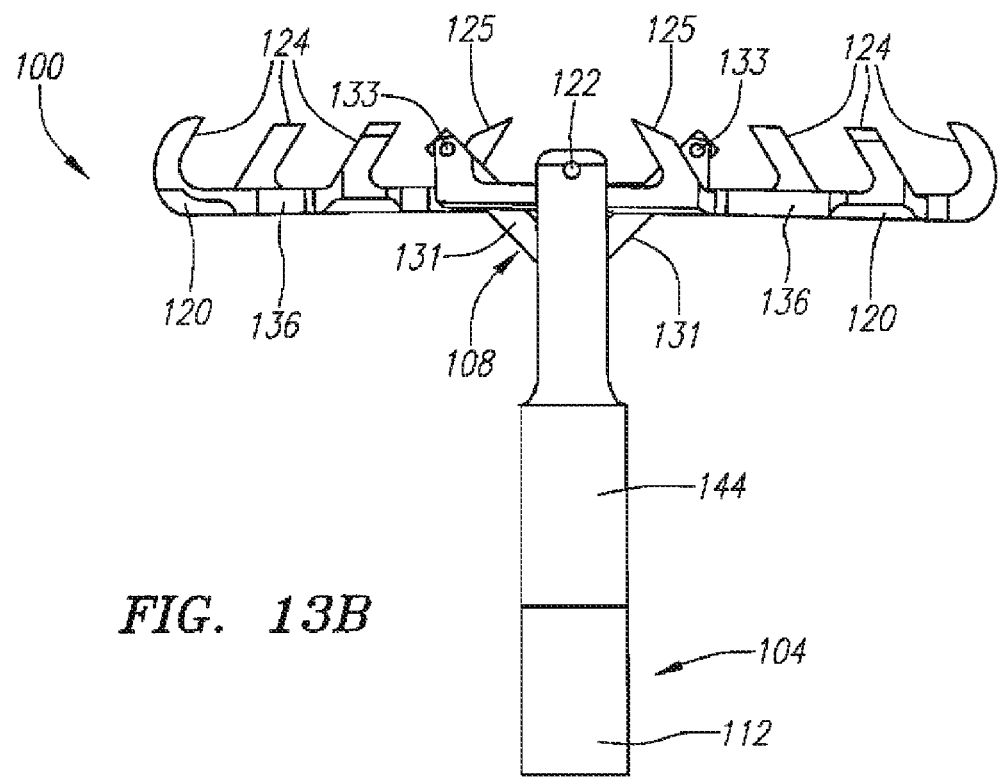
Figure 13C:
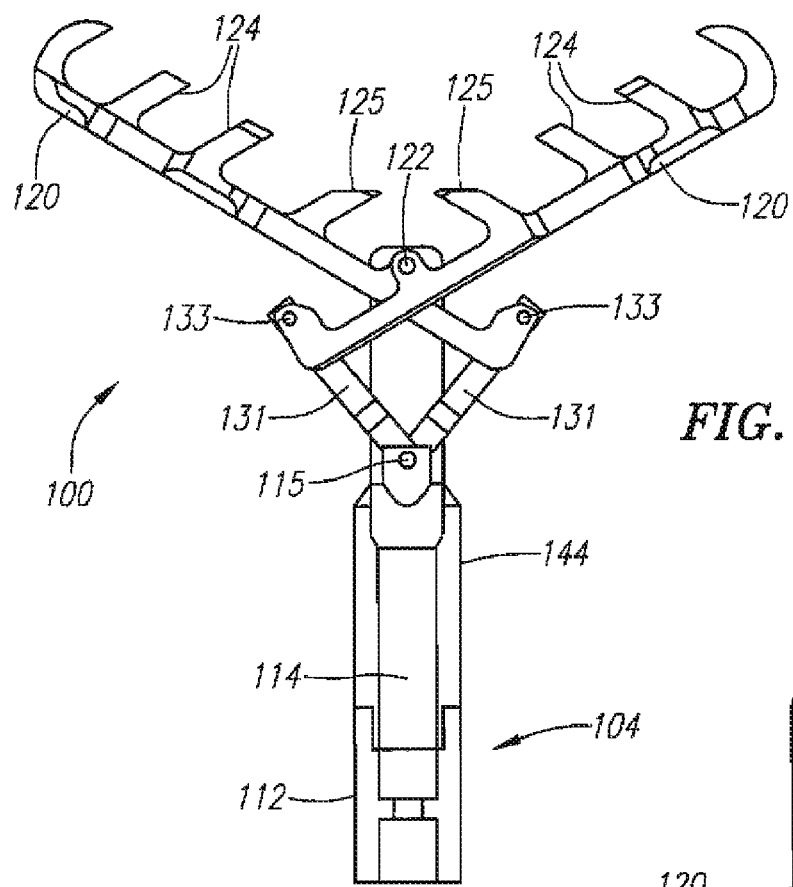
Figure 13D:
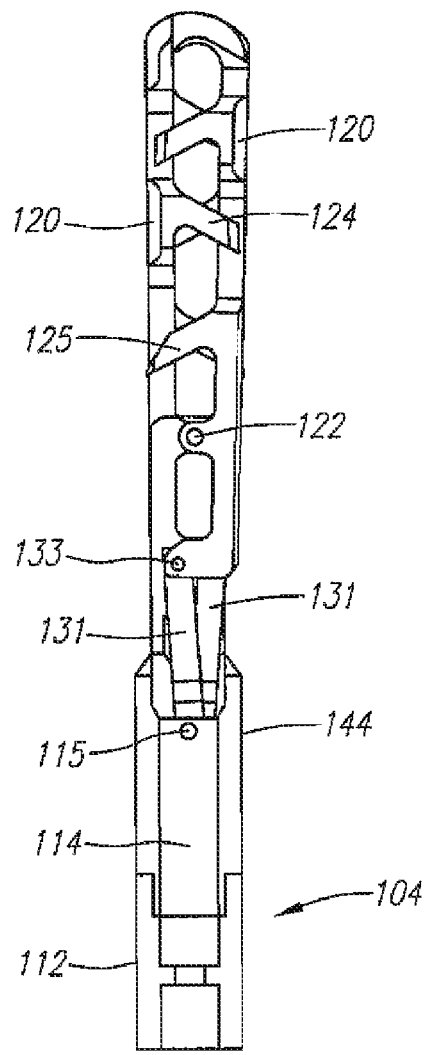

In another embodiment, shown in FIGS. 13A-D, the activation mechanism 108 includes a linkage assembly that is configured to move the jaws 120 between an open position having an included angle greater than 180 degrees (FIG. 13A) to a fully closed position in which the contact surfaces of the jaws 120 (or portions thereof) and/or the engagement members (e.g., teeth 124, 125) are in contact with one another (FIG. 13D). The linkage assembly includes a pair of links 131, each rotatably attached at one end by a pivot pin 115 to the distal end of the pusher 114 such that the links 131 are able to rotate about the axis defined by the pivot pin 115. Each link 131 is rotatably attached by another pivot pin 133 at its other end to one of the jaws 120. The jaws 120 are each rotatably attached by the pin 122 to a fork-shaped support member 144 that is attached or otherwise connected to the distal end of the shaft 104. The distance on each jaw 120 between the attachment point of each link 131 to each jaw 120 and the attachment point of each jaw 120 to the support 144 provides a lever arm for rotating the jaws 120 from the open to the closed position.

During operation, the user manipulates the controller (e.g., the handle 106) to cause the pusher 114 to advance (distally) or retract (proximally) relative to the sleeve 112 and the support member 144. This action causes the links 131 of the linkage assembly to be advanced and withdrawn, thereby causing the jaws 120 to move from the open to the closed position. For example, in FIG. 13A, the pusher 114 has been fully advanced (distally), causing each of the links 131 to be advanced distally and rotated radially away (i.e., around the pivot pin 115) from the longitudinal axis of the instrument. In the embodiment shown in FIG. 13A, the distal advancement of the links 131 is sufficient to cause the distal-most portion of the links 131 to extend distally of the tips of the vertex teeth 125 (and the non-vertex teeth 124). In an embodiment, the distal-most portion of each of the links 131 is provided with a blunt or otherwise atraumatic shape, thereby creating a generally atraumatic state for the medical instrument in the fully open position due to the vertex teeth 125 being effectively hidden behind the extended links 131, as shown in FIG. 13A. In the atraumatic state shown, the medical instrument is able to be pushed against tissue with minimal or no tearing or puncturing of the tissue by the vertex teeth 125.

As the user manipulates the controller to retract the pusher 114 proximally relative to the sleeve 112 and support 144, the links 131 are also retracted and are simultaneously caused to rotate around the pivot pin 115 radially toward the longitudinal axis of the shaft 104. This movement cause the jaws 120 to move toward the closed position, as shown in FIGS. 13B through 13D. At the position shown in FIG. 13B, the jaws 120 have moved to a position corresponding to an included angle of approximately 180 degrees. The vertex teeth 125 have moved to a point relative to the links 131 that they extend distally of the links, in a position adapted to engage tissue. Further retraction of the pusher 114 causes the jaws to rotate to the positions shown in FIG. 13C and, finally, to the closed position shown in FIG. 13D.

Figure 5:
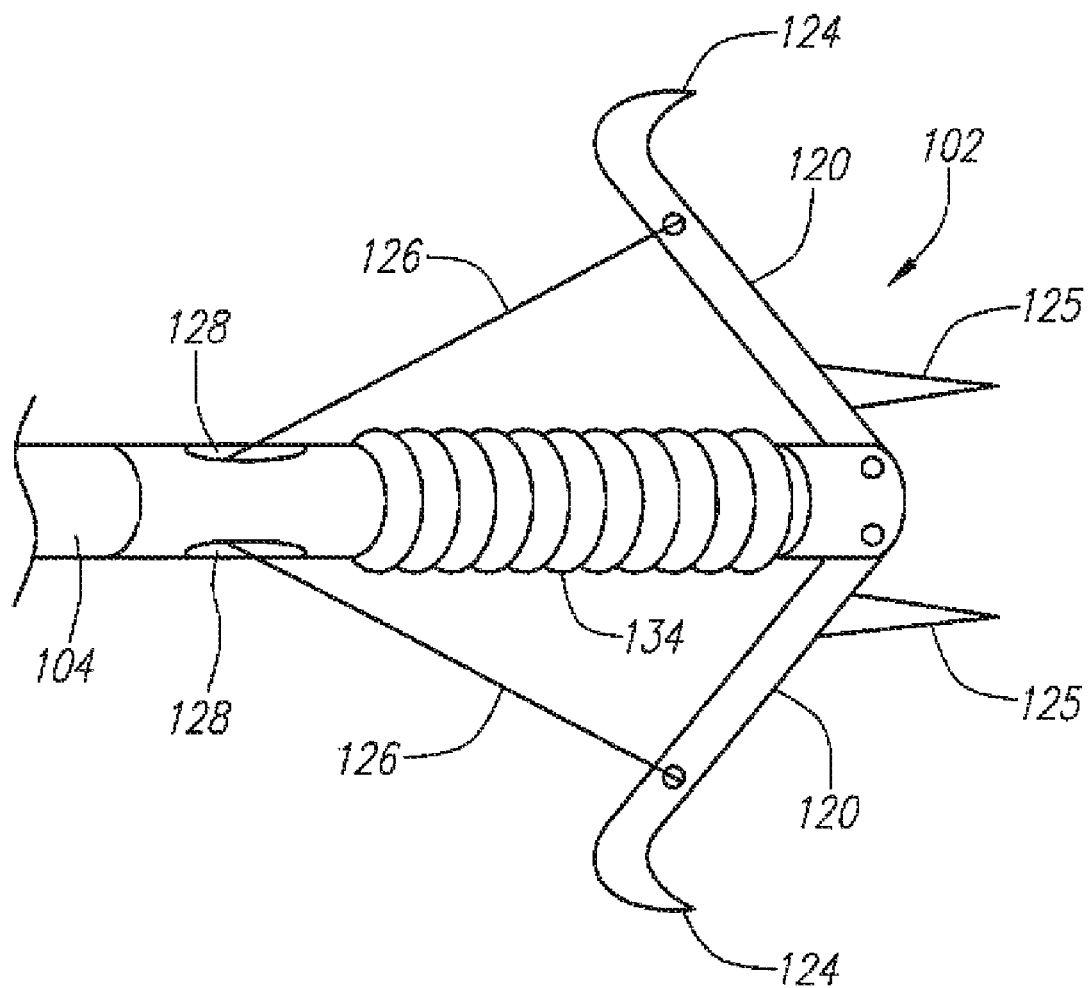
FIG. 5 is a side view of another embodiment of a tissue grasping member and activation mechanism.

In the embodiments described above, the distal portion of the medical instrument includes components that are formed of relatively rigid materials, including the jaws 120. These relatively rigid portions of the medical instrument are relatively more difficult to load and remove through small diameter tool lumens commonly used during endoscopic, laparoscopic, or translumenal procedures. Accordingly, in an embodiment illustrated in FIG. 5, a distal portion of the shaft 104 located between the drive wire exit ports 128 and the distal end of the shaft 104 is constructed to be relatively flexible in order, for example, to facilitate the transmission of the instrument through these types of tool lumens. In the embodiment shown, the flexible shaft region 134 is formed of a coil body having a relatively high degree of flexibility. The skilled artisan will recognize that other known materials and constructions are suitable to obtain the desired degree of flexibility.

Figure 6A:
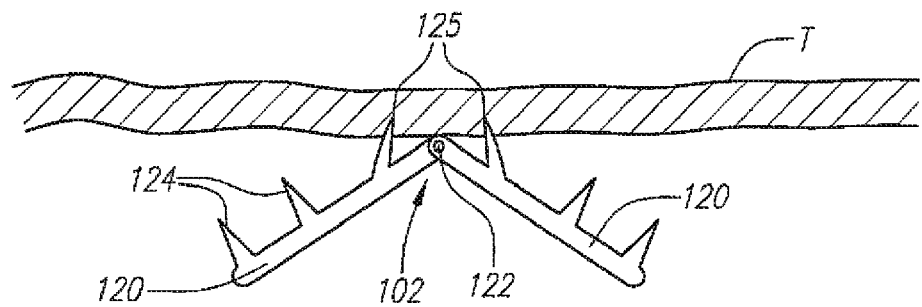
FIGS. 6A-D are side views of another embodiment of a tissue grasping member.
Figure 6B:
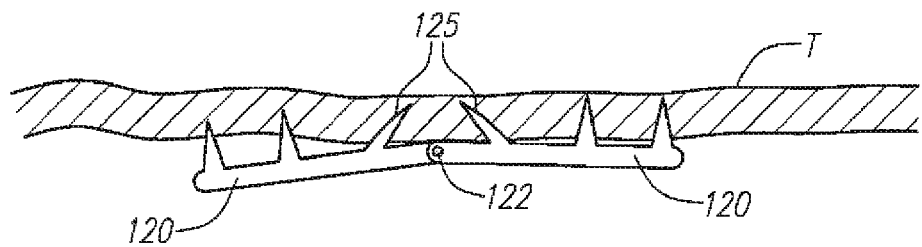
Figure 6C:
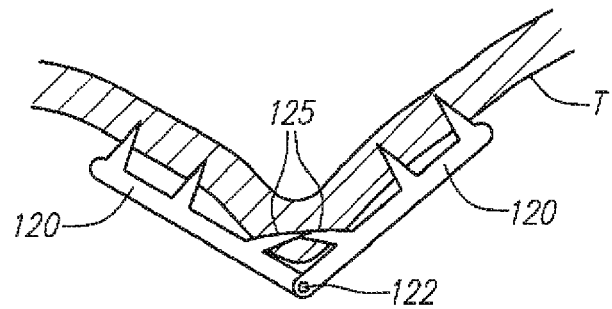
Figure 6D:
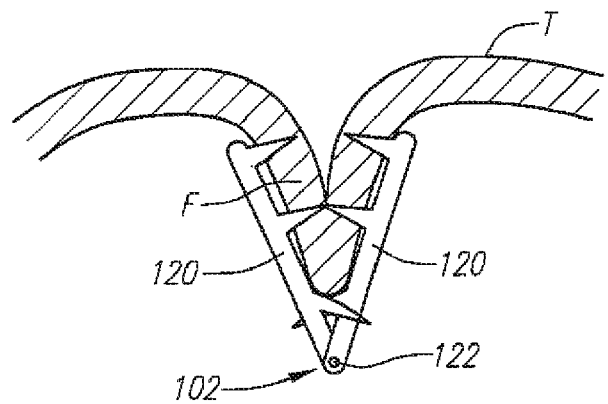

Turning to FIGS. 6A-D, the Figures illustrate the action of an embodiment of a pair of jaws 120 engaging a portion of patient tissue T as the jaws move from an open position having an included angle greater than 180 degrees (FIG. 6A) to a nearly closed position (FIG. 6D). For clarity, only the jaws 120 of the medical instrument 100 are shown in FIGS. 6A-D, it being understood that the jaws 120 are incorporated within a medical instrument consistent with one or more of the embodiments described herein. As shown in FIGS. 6A-D, the vertex teeth 125 of each jaw 120 are configured to increase the ability of the jaws 120 to create an inverted tissue fold, in relation to the ability of a conventional grasper to create such folds. For example, in the embodiment shown, the vertex teeth 125 are formed on the contact surfaces of the respective jaws and are oriented such that they are angled inwardly toward the vertex formed by the jaws 120, i.e., the vertex teeth 125 each generally form an included angle less than 90 degrees with respect to the portion of the contact surface of the jaws 120 that lies between the vertex tooth 125 and the pivot point 122 of the jaw. Although the embodiment shown in FIGS. 6A-D shows the entire vertex tooth 125 forming the included angle less than 90 degrees, in other embodiments, the angle is formed only by the peak portion 125a or another portion of the vertex teeth 125.

Turning first to FIG. 6A, the jaws 120 are shown in a fully opened position in which the included angle between the jaws is greater than 180 degrees. The vertex teeth 125 of the jaws are oriented such that they are able to penetrate the tissue T as the medical instrument is advanced to engage the jaws 120 with the tissue T with the jaws in the fully opened position. Conversely, the remaining teeth 124 are oriented such that they are set off from the tissue relative to the vertex teeth 125. Turning next to FIGS. 6B-D, as the jaws close, the vertex teeth 125 rotate about the pivot axis to draw tissue into the vertex of the jaws, thereby transitioning from a tissue penetrating orientation to a tissue engaging orientation. The remaining teeth 124 on the jaws 120 engage the tissue as the jaws are closed. In this way, a tissue fold F (see FIG. 6D) is formed. The tissue fold F will typically be deeper and more robust than a tissue fold formed using a comparably sized conventional grasper. For example, the tissue fold F will typically include more of the tissue underlying the top surface of the tissue T than is gathered using a conventional grasper.

Figure 7A:
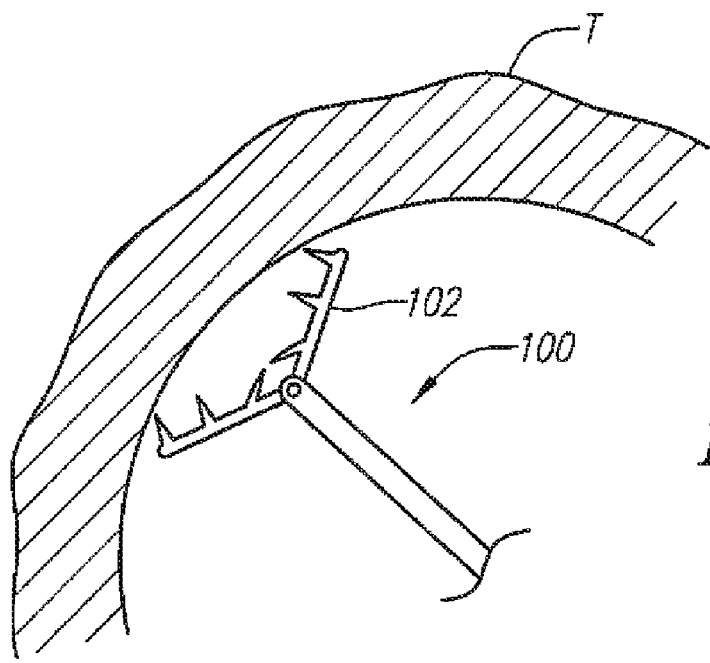
FIG. 7A is a side view of a medical instrument having a tissue grasping member defining an included angle of less than 180 degrees.
Figure 7B:
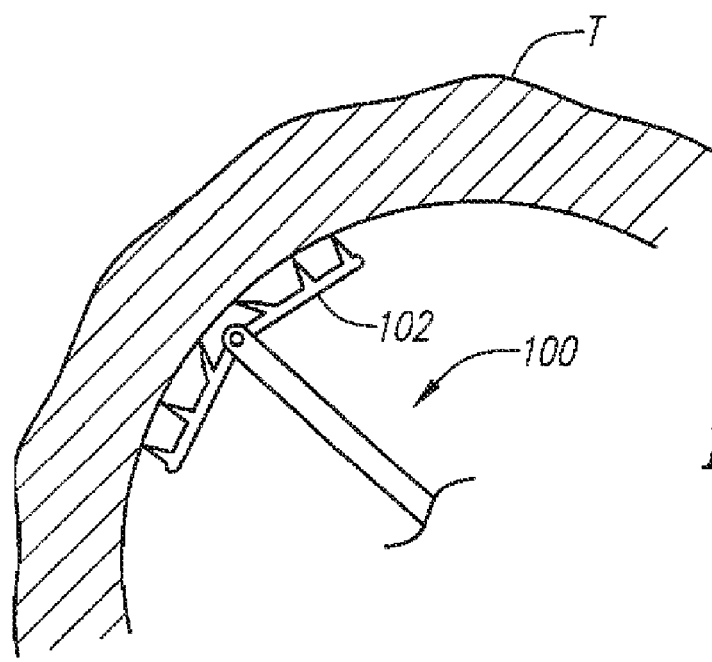
FIG. 7B is a side view of a medical instrument having a tissue grasping member defining an included angle of greater than 180 degrees.

FIGS. 7A-B illustrate an additional advantage obtained by embodiments of the medical instruments described herein. The Figures illustrate two medical instruments located adjacent to a portion of tissue T having a concave facing surface, such as the internal surface of a curved hollow body organ such as the stomach. The first medical instrument, shown in FIG. 7A, includes a pair of operable jaws that open to an included angle of less than 180 degrees, such as the case with a conventional laparoscopic grasper. The second medical instrument, shown in FIG. 7B, is configured such that its pair of operable jaws open to an included angle of greater than 180 degrees, such as the case of several embodiments of the medical instruments 100 described herein. As shown in the Figures, the opened jaws of the second medical instrument (FIG. 7B) more closely conform to the concave profile of the tissue due to the ability of the jaws to open to the larger included angle of greater than 180 degrees. This feature allows the jaws to more readily grasp tissue and to form deeper tissue folds, as described above in relation to FIGS. 6A-D, particularly in situations such as those encountered within a curved, hollow body organ.

Figure 8A:
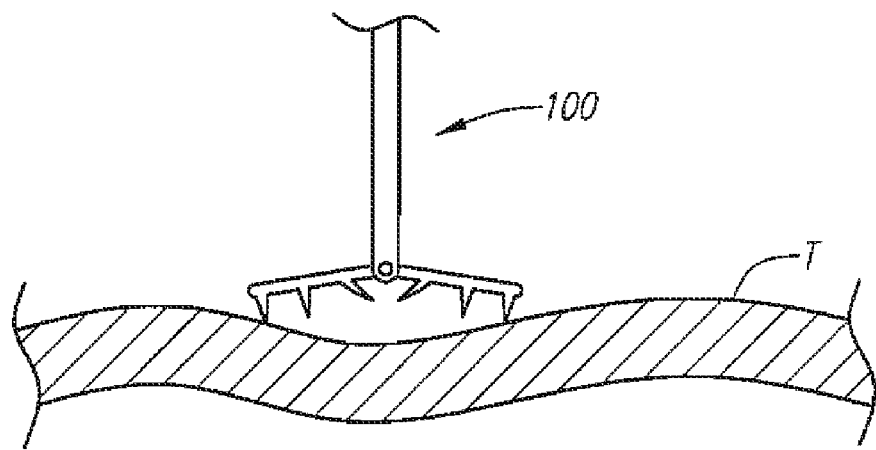
FIGS. 8A-C are side views of a medical instrument engaging and grasping tissue.
Figure 8B:
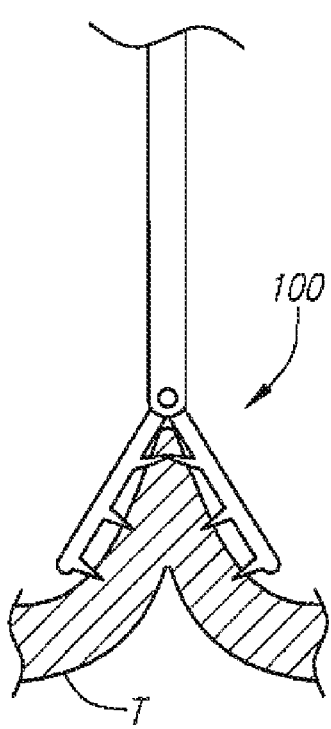
Figure 8C:
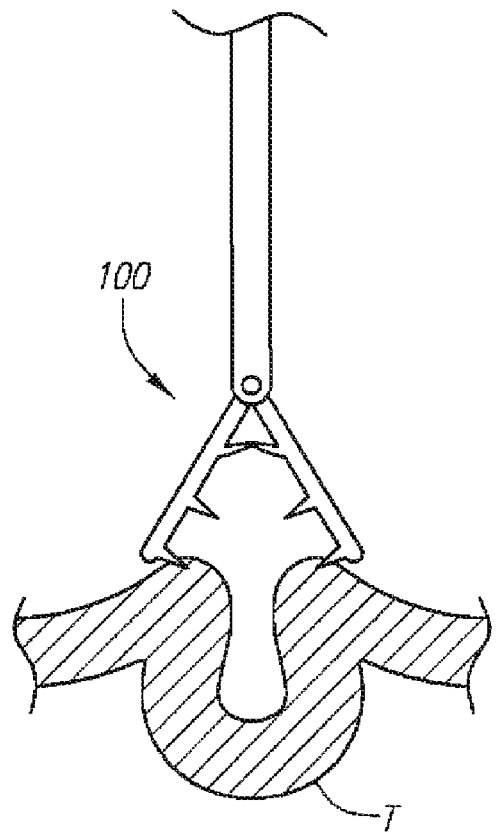

FIGS. 8A-C illustrate an additional advantage obtained by several of the embodiments of the medical instruments described herein. As described above in relation to FIGS. 7A-B, when procedures are performed within a hollow body organ or other tissue location in which the tissue presents as a concave surface, conventional graspers do not engage, grasp, and manipulate tissue well. This situation is made even more difficult when the hollow body organ is pressurized, such as by insufflation. In addition, when tissue is grasped by conventional graspers, it frequently occurs that the peripheral tips of the grasper jaws engage tissue but the interior portions do not, with the result that a portion of tissue is likely to evert (as shown in FIG. 8C) rather than invert (as shown in FIG. 8B). As described above in relation to FIGS. 6A-D, a medical instrument 100 having vertex teeth 125 that are angled toward the pivot point of the jaws 120 is adapted to engage tissue and to form deep tissue folds. An embodiment of such a medical instrument 100 is shown in FIGS. 8A and 8B, and is configured to more readily cause the grasped tissue to invert, thereby forming a deep tissue fold.

Figure 9:
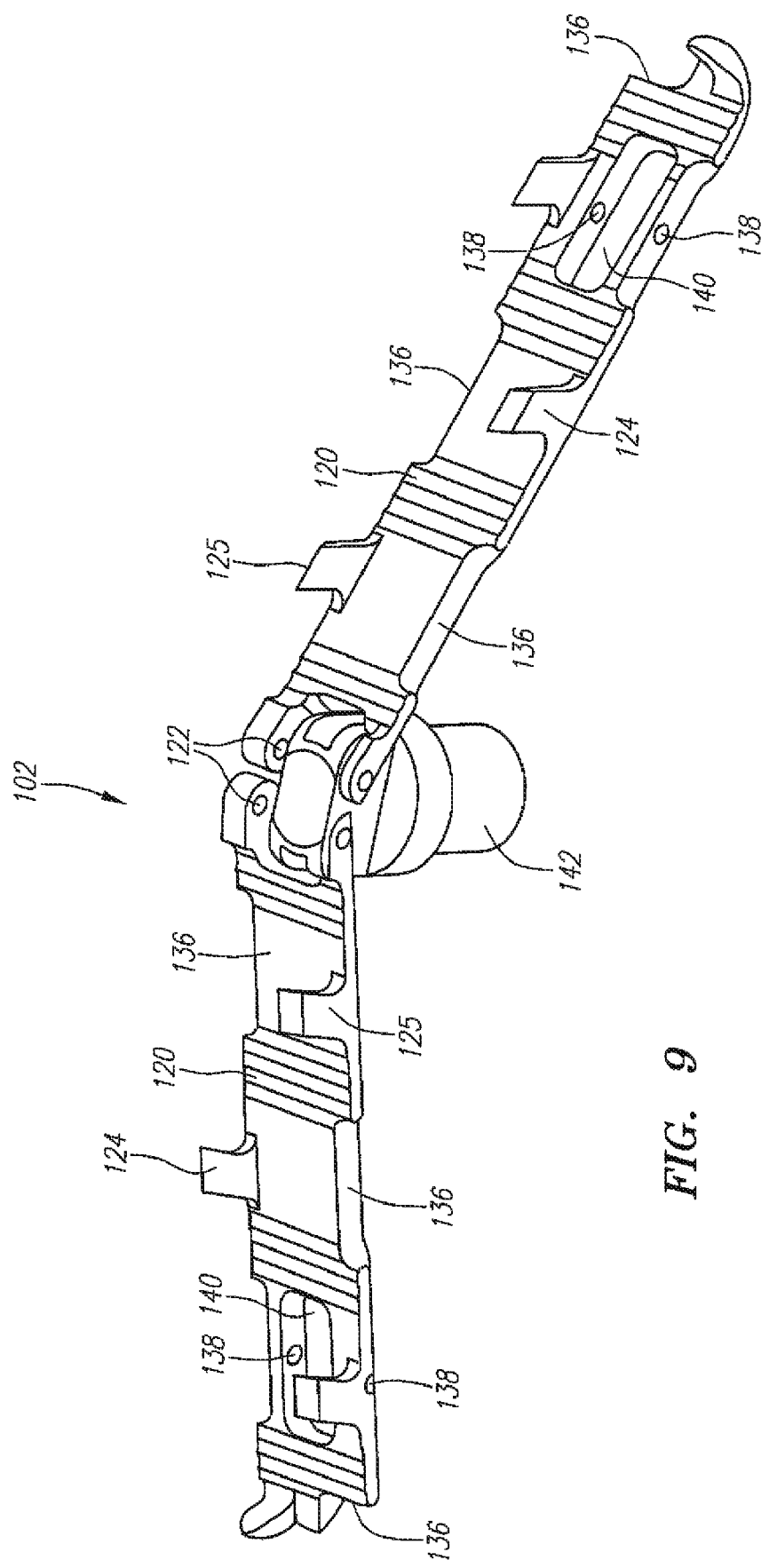
FIG. 9 is a perspective view of another embodiment of a tissue grasping member.
Figure 10A:
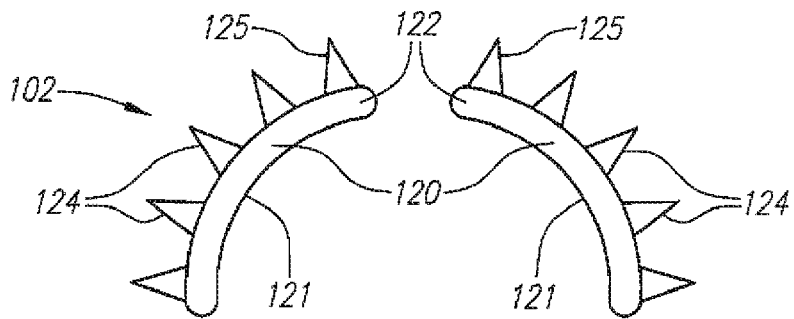
FIGS. 10A-D are side views of another embodiment of a tissue grasping member.
Figure 10B:
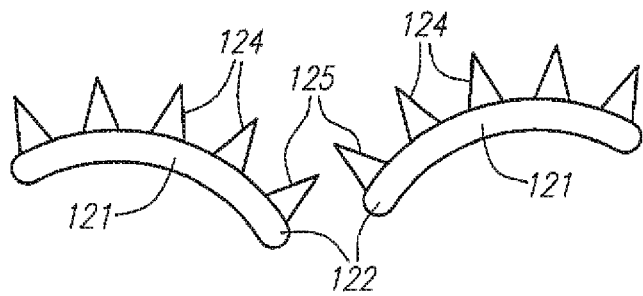
Figure 10C:
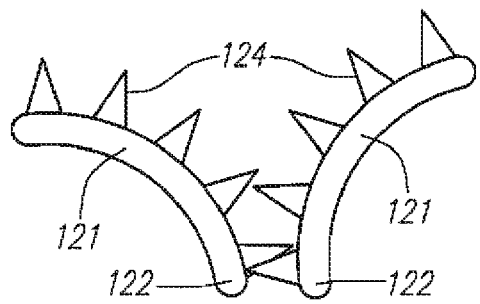
Figure 10D:
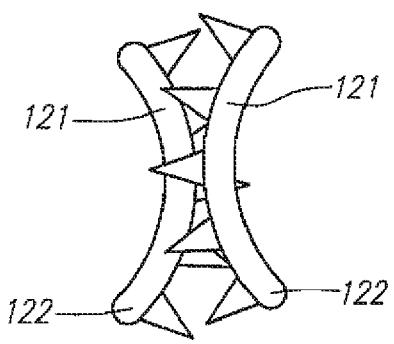

Turning to FIG. 9, there is shown another embodiment of a pair of jaws 120 forming a portion of a tissue grasping member 102 of a medical instrument 100. For clarity, the shaft 104 and activation mechanism 108 are not shown in the Figure, it being understood that the jaws 120 are adapted to be incorporated within one or more of the medical instrument embodiments described herein. Each jaw 120 is pivotably attached to a post 142 using a pivot pin or other suitable connector. The post 142 is configured to be attached or otherwise connected to the distal end of a shaft 104. As described above, each jaw 120 is capable of pivoting around the post 142 such that the pair of jaws 120 forms an included angle of greater than 180 degrees. Each of the jaws 120 includes a vertex tooth 125, with the vertex teeth 125 being staggered relative to one another in order to facilitate closing of the jaws 120. Each vertex tooth 125 is formed on the surface of its respective jaw 120 such that it defines an included angle of less than 90 degrees with respect to the contact surface of the jaw. In the embodiment shown in FIG. 9, each of the other teeth 124 formed on the jaws 120 also form an acute included angle relative to the contact surface of its respective jaw 120. Each jaw 120 includes a plurality of recesses 136 formed on the sides opposite the non-vertex teeth 124 and vertex tooth 125 in order to accommodate the non-vertex teeth 124 and vertex tooth 125 of the opposed jaw when the jaws are closed, thereby reducing the profile of the tissue grasping member 102 when the jaws are closed. In an embodiment, each jaw 120 also includes a pair of side holes 138 and a pocket 140 used to attach a pivot 132 (see FIGS. 2, 4A-B) or other member providing an interconnection between the jaw 120 and the activation mechanism 108.

Turning to FIGS. 10A-D, there is shown another embodiment of a pair of jaws 120 forming a portion of a tissue grasping member 102 of a medical instrument 100. As stated above, for clarity, only the jaws 120 are shown in the Figure. Each jaw 120 includes a curved base portion 121 causing the contact surface to have a generally convex shape. The jaws 120 are adapted to rotate around their respective pivot points 122, similarly to the manner described above in relation to the embodiment shown in FIG. 2. The curved jaws 120 allow the tips of the jaws 120 to be positioned at points comparable to in included angle greater than 180 degrees when the vertex is opened to a point comparable to an included angle of approximately 180 degrees, as shown, for example, in FIG. 10A. Accordingly, the teeth 124, 125 formed relatively normal to the jaws 120 are able to grasp and obtain deep tissue folds in a manner similar to that described for the previous embodiments. The curved jaws 120 operate in a manner comparable to a pair of opposed gears to draw tissue between the jaws and acquire deep tissue folds.

Figure 11A:
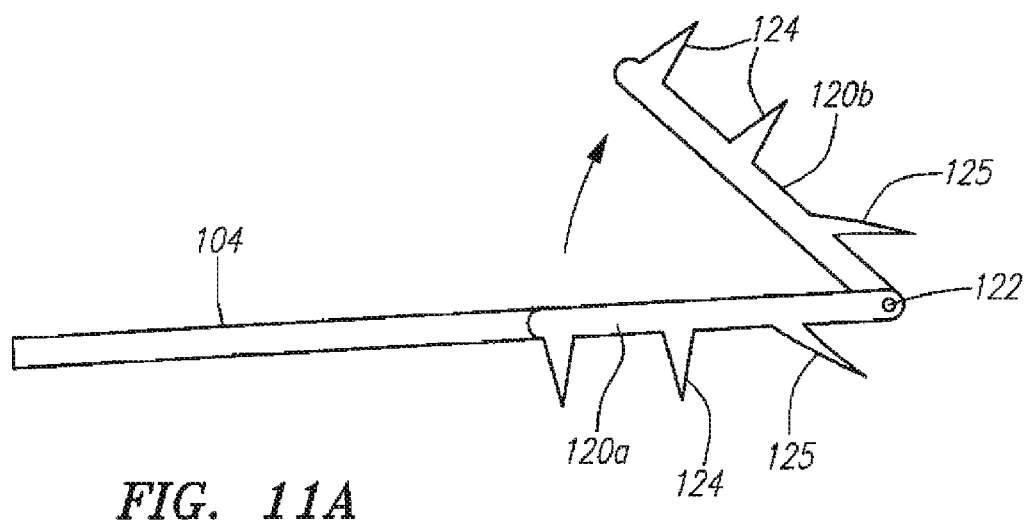
FIGS. 11A-C are side views of another embodiment of a tissue grasping member attached to a shaft.
Figure 11B:
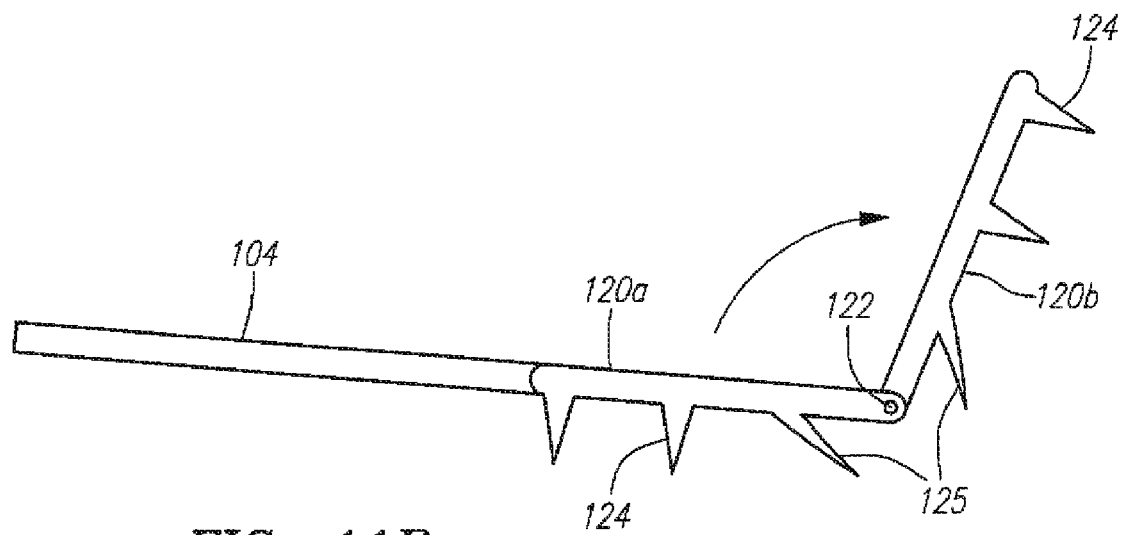
Figure 11C:
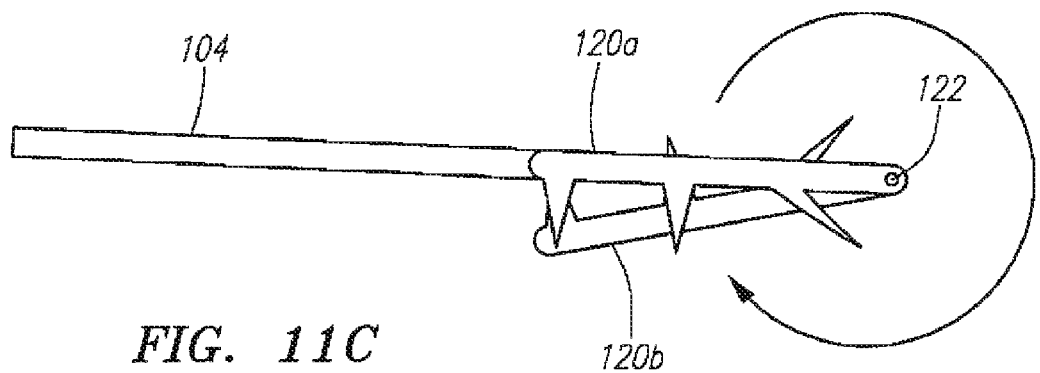

Turning to FIGS. 11A-C, there is shown another embodiment of a pair of jaws 120 forming a portion of a tissue grasping member 102 of a medical instrument 100. A shaft 104 is also shown in the Figures, though, for clarity, the control member and activation member are not shown. In the embodiment shown in FIGS. 11A-C, the jaws 120 operate using a "side on" directionality and include a first, fixed jaw 120a and a second, movable jaw 120b. The "side on" directionality includes engaging and manipulating tissue from a side approach relative to the axis of the shaft, rather than the direct or "head on" approach used in the embodiments described above. This directionality is obtained by pivotably attaching the movable jaw 120b to the fixed jaw 120a at a pivot point 122 on end of the fixed jaw 120a opposite the end to which the shaft is attached to the fixed jaw 120a. Each jaw is provided with engagement teeth 124, including a vertex tooth 125. The movable jaw 120b is adapted to rotate around its pivot point 122 under the force of the activation mechanism (not shown) to engage, penetrate, and manipulate tissue, such as to form a tissue fold.

Figure 12A:
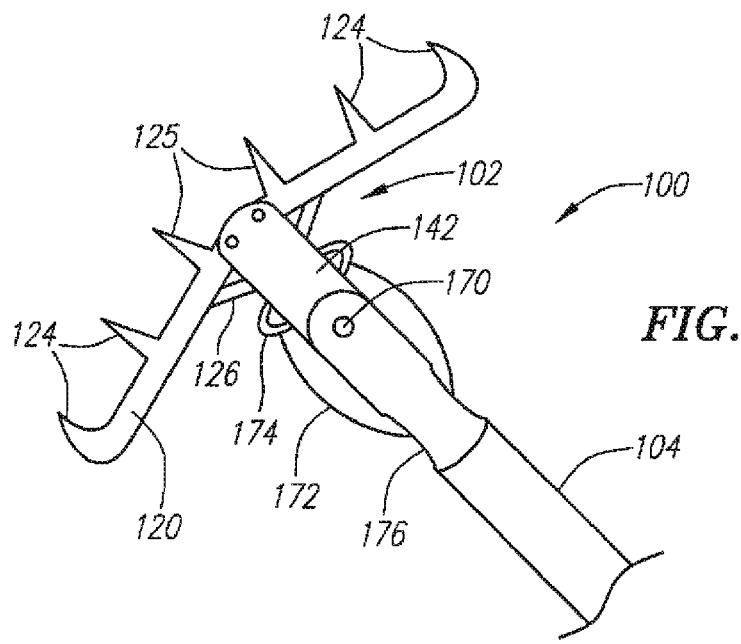
FIGS. 12A-C are side views of additional embodiments of tissue grasping members attached to a shaft and having a steering mechanism.
Figure 12B:
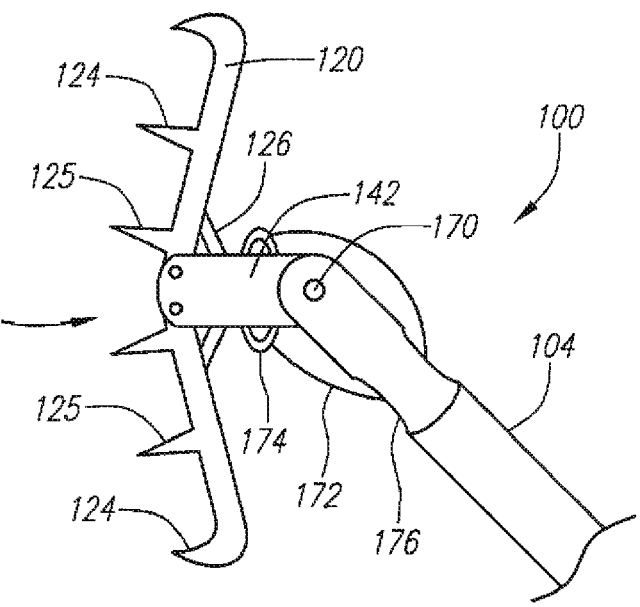
Figure 12C:
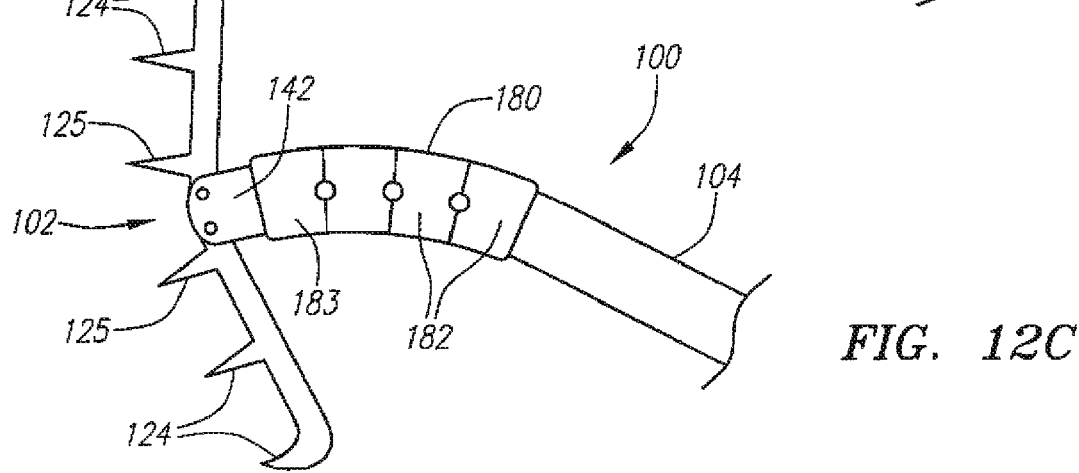

FIGS. 12A-C illustrate additional embodiments of medical instruments 100 having tissue grasping members 102 formed on the distal end of an elongated, flexible shaft 104. Each of the embodiments shown in FIGS. 12A-C includes a steering mechanism configured to steer the tissue grasping member 102 in one or more planes. The steering motion may be used, for example, to move the tissue grasping member 102 into an optimal position to grasp tissue. The steering capability may be used as the only steering mechanism for the medical instrument 100, or it may be used in addition to other steering mechanisms contained on the medical instrument 100 or in an overtube or other accessory used in association with the medical instrument.

For example, in FIGS. 12A-B, the tissue grasping member 102 is pivotably attached to the distal end of the shaft 104 by a hinge 170. In the embodiment shown, the hinge 170 includes a pin inserted through holes formed in each of the tissue grasping member 102 and the distal end of the shaft 104. Other hinge structures are used in alternative embodiments. A pair of drive wires 172 extend through a pair of exit ports 176 formed on the shaft 104, and connect at their distal ends to a pair of pivots 174 formed on the tissue grasping member 102. The drive wires 172 extend proximally to the controller, such as the handle 106, where the user is able to control the steering movement of the tissue grasping member 102 relative to the shaft 104 by advancing (distally) and/or withdrawing (proximally) the drive wires 172. The advancing and withdrawing motions of the drive wires 172 cause the tissue grasping member 102 to rotate about the hinge 170, thereby allowing the user to move the tissue grasping member 102 into a preferred position relative to the tissue.

In another embodiment, shown in FIG. 12C, the steering mechanism is a flexible steering section 180 including a plurality of links 182 pivotably connected to each adjacent link. One or more pull wires (not shown) extend from the controller (e.g., the handle 106) to the distal-most link 183, whereby the pull wires are able to be advanced and/or retracted to steer the tissue grasping member 102 attached to the distal end of the steering section 180. In an embodiment, the pull wires are contained on the interior of the plurality of links 182. In alternative embodiments, the pull wires are contained on the exterior of the plurality of links 182, or the pull wires extend through longitudinal holes or slots formed in the individual links 182.

The medical instruments described herein are adapted for use in engaging, grasping, and manipulating tissue during open surgery, laparoscopic surgery, endoscopic surgery, or translumenal surgery. In particular, the medical instruments are adapted to engage the soft, multilayer tissue of a human or animal stomach in an endolumenal approach. Alternatively, the medical instruments may be used to engage other human or animal gastric tissue, peritoneal organs, external body surfaces, or tissue of the lung, heart, kidney, bladder, or other body tissue. The instruments are particularly useful for engaging, grasping, and manipulating tissue that is difficult to engage using conventional graspers, which frequently occurs during translumenal surgical procedures (e.g., natural orifice translumenal endoscopic surgery, or "NOTES"). Several translumenal procedures are described in U.S. patent applications Ser. Nos. 10/841,233, 10/898,683, 11/238,279, 11/102,571, 11/342,288, and 11/270,195, which are hereby incorporated by reference. The medical instruments described herein are suitable for use in combination with, for example, the endoluminal tool deployment systems described in U.S. patent application Ser. No. 10/797,485, which is hereby incorporated by reference. In particular, the tool deployment systems described in the '485 application includes one or more lumens suitable for facilitating deployment of the medical instruments described herein to perform or assist in performing endoscopic, laparoscopic, or NOTES diagnostic or therapeutic procedures. In addition, the medical instruments described herein are suitable for use in combination with, or instead of, the methods and instruments described in U.S. patent application Ser. No. 11/412,261, which is also incorporated by reference herein.

Although various illustrative embodiments are described above, it will be evident to one skilled in the art that various changes and modifications are within the scope of the invention. It is intended in the appended claims to cover all such changes and modifications that fall within the true spirit and scope of the invention.

What is claimed is:

1. Apparatus for grasping tissue comprising:
   a control member;
   a tissue grasping member;
   an activation mechanism responsive to said control member and operatively coupled to said tissue grasping member; and
   an elongated flexible member extending between and coupled to each of said control member and said tissue grasping member;
   wherein said tissue grasping member comprises a first member having a proximal end pivotably attached to said elongated flexible member and having a distal end and a first contact surface, and a second member having a proximal end pivotably attached to said elongated flexible member and having a distal end and a second contact surface, said first and second contact surfaces defining an included angle of 180 degrees or more;
   wherein said activation mechanism comprises a first drive wire attached to said first member at a location nearer to the distal end than the proximal end of the first member and adapted to move said first member around its pivotable attachment to said elongated flexible member; and
   wherein said activation mechanism further comprises a second drive wire attached to said second member at a location nearer to the distal end than the proximal end of the second member and adapted to move said second member around its pivotable attachment to said elongated flexible member.

2. The apparatus of claim 1, wherein said control member comprises a handle.

3. The apparatus of claim 2, wherein said handle comprises a ratcheting mechanism.

4. The apparatus of claim 2, wherein said handle comprises a pusher block slidably received within a main body, and an actuation arm connected to said pusher block by a linkage.

5. The apparatus of claim 1, wherein said first member comprises a first jaw and said second member comprises a second jaw.

6. The apparatus of claim 5, wherein said first jaw includes an engagement member that defines an acute angle relative to a contact surface of said first jaw.

7. The apparatus of claim 6, wherein said second jaw includes an engagement member that defines an acute angle relative to a contact surface of said second jaw.

8. The apparatus of claim 5, wherein said first jaw includes a plurality of teeth.

9. The apparatus of claim 8, wherein said second jaw includes at least one recess adapted to receive at least one of said plurality of teeth.

10. The apparatus of claim 1, wherein said elongated flexible member comprises a shaft having a sleeve and a pusher.

11. The apparatus of claim 10, wherein said pusher comprises at least two elongated members.

* * * * *